United States Patent [19]

Okazaki

[11] Patent Number: 5,165,412

[45] Date of Patent: Nov. 24, 1992

[54] SHOCK WAVE MEDICAL TREATMENT APPARATUS WITH EXCHANGEABLE IMAGING ULTRASONIC WAVE PROBE

[75] Inventor: Kiyoshi Okazaki, Tochigi, Japan

[73] Assignee: Kabushiki Kaisha Toshiba, Kawasaki, Japan

[21] Appl. No.: 807,617

[22] Filed: Dec. 13, 1991

Related U.S. Application Data

[63] Continuation of Ser. No. 487,053, Mar. 5, 1990, abandoned.

[51] Int. Cl.⁵ .............................................. A61B 17/22
[52] U.S. Cl. .......................... 128/660.03; 128/24 EL
[58] Field of Search ........................ 128/660.03, 24 EL

[56] References Cited

U.S. PATENT DOCUMENTS

| | | | |
|---|---|---|---|
| 4,787,394 | 11/1988 | Ogura | 128/660.03 |
| 4,928,672 | 5/1990 | Grasser et al. | 128/24 |
| 4,957,099 | 9/1990 | Hassler | 128/660.03 |
| 4,957,830 | 8/1990 | Rattner et al. | 128/24 EL |

FOREIGN PATENT DOCUMENTS

| | | |
|---|---|---|
| 316863 | 5/1989 | European Pat. Off. . |
| 3826709 | 2/1989 | Fed. Rep. of Germany ...................... 128/660.03 |
| 3900893 | 8/1989 | Fed. Rep. of Germany . |
| 2587493 | 3/1987 | France . |

Primary Examiner—Ruth S. Smith
Attorney, Agent, or Firm—Foley & Lardner

[57] ABSTRACT

A shock wave medical treatment apparatus in which the imaging ultrasonic wave probe can be changed among those of different imaging region depths easily. The apparatus includes a shock wave transducer for generating shock waves with a focal point inside a body to be treated, having an aperture at a center; an imaging ultrasonic wave probe for taking images of the body to be treated containing the focal point of the shock wave; and a housing pipe, placed on a line joining the focal point of the shock wave and a center of the aperture of the shock wave transducer, for exchangeably holding the imaging ultrasonic wave probe.

6 Claims, 8 Drawing Sheets

SHOCK WAVE MEDICAL TREATMENT APPARATUS WITH EXCHANGEABLE IMAGING ULTRASONIC WAVE PROBE

This application is a continuation of application Ser. No. 07/487,053, filed Mar. 5, 1990 now abandoned.

BACKGROUND OF THE INVENTION

1. Field of the Invention

The present invention relates to a shock wave medical treatment apparatus for treating an object to be treated inside a patient, such as a cancer cell or concretion, by disintegrating them by means of the focusing energy of a shock wave.

2. Description of the Background Art

Figure 1:
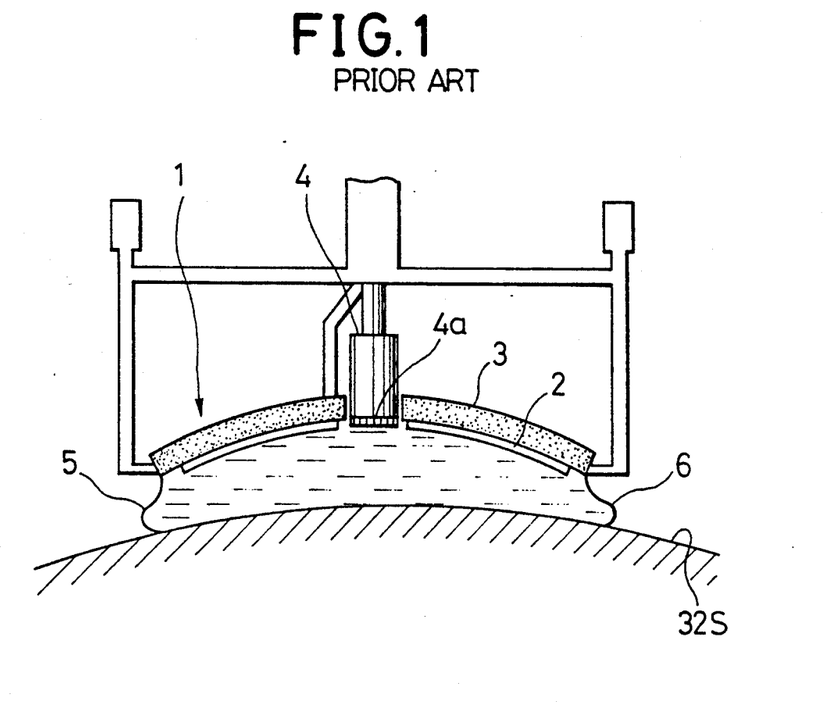
FIG. 1 is a schematic cross sectional view of one example of a conventional shock wave medical treatment apparatus.

An example of a conventional shock wave medical treatment apparatus, an ultrasonic wave applicator disclosed in Japanese Patent Application Laid Open No. 62-049843 (1987), is shown in FIG. 1.

This ultrasonic wave applicator 1 comprises a concave oscillator 2 of 10 cm diamter and a constant curvature for generating focused ultrasonic waves which has an aperture of a prescribed shape at its middle, a backing material 3 uniformly attached to a back of this concave oscillator 2, an imaging ultrasonic wave probe 4 for taking images of region to be treated by transmitting and receiving imaging ultrasonic waves, which is fixed at the aperture of the concave oscillator 2 and which is a sector scanning type having an array 4a of minute oscillator elements at a bottom face, and an acoustic coupler 5 for propagating the focused ultrasonic waves from the concave oscillator 2 to a surface 32S of a patient which is made of a bag 6 of thin film having an acoustic impedance substantially equal to that of water and which is filled with water.

In this ultrasonic wave applicator 1, the array 4a of the oscillator elements of the imaging ultrasonic wave probe 4 is either aligned with a curved ultrasonic wave generating surface of the concave oscillator 2 or placed further away from the surface 32S of the patient than the curved ultrasonic wave generating surface of the concave oscillator 2.

In such a configuration, the imaging ultrasonic waves to be transmitted and received by the imaging ultrasonic wave probe 4 inevitably suffer from scattering and dissipation due to the intervening water inside the acoustic coupler 5 and the thin film of the bag 6. For this reason, the images to be displayed by a display unit (not shown) are influenced by noise so that locating the object to be treated becomes difficult.

Figure 2:
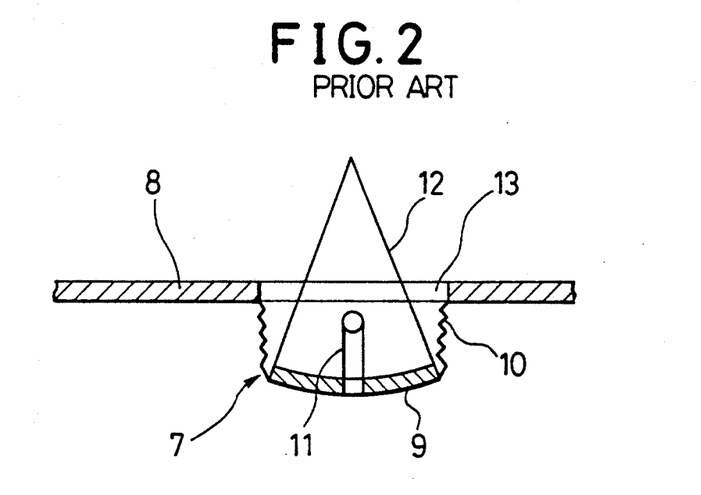
FIG. 2 is a schematic cross sectional view of another example of a conventional shock wave medical treatment apparatus.

On the other hand, an alternative configuration for the ultrasonic wave applicator is shown in FIG. 2.

This ultrasonic wave applicator 7 comprises a concave oscillator 9 for generating ultrasonic waves of focusing trajectory 12 which is similar to the concave oscillator 2 of the previous example described above and which is located below a bed 8, a water bag 10 filled with water for transmitting the ultrasonic waves which is provided between an ultrasonic wave generating surface of the concave oscillator 9 and an opening 13 of the bed 8 located above the concave oscillator 9, and a mechanical probe 11 placed inside the water bag 10 which has a fixed focal length.

In this alternative configuration, the problem of scattering and dissipation as described above for the previous example is also present. In addition, there are problems, due to the fact that the probe 11 is a mechanical probe, such as deterioration of image quality, enlargement of the configuration, and vulnerability to vibrations. Moreover, in the configuration of FIG. 2, operation of the ultrasonic wave applicator 7 is harder because this ultrasonic wave applicator 7 is fixed to the bed 8.

To deal with such problems of a conventional shock wave medical treatment apparatus, the present inventor has proposed a shock wave applicator comprising a shock wave transducer for generating shock waves with a focal point located inside a patient, a water bag provided at a shock wave generating surface of the shock wave transducer, and an imaging ultrasonic transducer located between the shock wave generating surface and the focal point for taking image data of the patient in a region including the focal point in a state of contacting its ultrasonic wave transmitting and receiving surface to a surface of the patient, as disclosed in Japanese Patent Application Laid Open No. 62-290158 (1987).

Now, in general, the distance from a body surface to the object to be treated varies according to the organ containing the object to be treated and depending on whether the patient is an adult or child. Moreover, dissipation of the ultrasonic wave varies, depending on the physical constitution of the patient.

For these reasons, there arises a necessity to change the imaging ultrasonic wave probe to that of different characteristics in accordance with the distance of the object to be treated from the body surface and the physical constitution of the patient.

However, exchangeability of the imaging ultrasonic wave probe has not been considered in the conventional shock wave medial treatment apparatus, so that the imaging ultrasonic wave probe could not be easily changed.

SUMMARY OF THE INVENTION

It is therefore an object of the present invention to provide a shock wave medical treatment apparatus in which the imaging ultrasonic wave probe can be changed among those of different imaging region depths, so that locating of the object to be treated inside the patient becomes easier.

This object is achieved in the present invention by providing a shock wave medical treatment apparatus, equipped with a shock wave applicator comprising: shock wave transducer means for generating shock waves with a focal point inside a body to be treated, having an aperture at a center; imaging ultrasonic wave probe means for taking images of the body to be treated containing the focal point of the shock wave; and housing pipe means, placed on a line joining the focal point of the shock wave and a center of the aperture of the shock wave transducer means, for exchangeably holding the imaging ultrasonic wave probe means.

Other features and advantages of the present invention will become apparent from the following description taken in conjunction with the accompanying drawings.

DETAILED DESCRIPTION OF THE PREFERRED EMBODIMENTS

Figure 3:
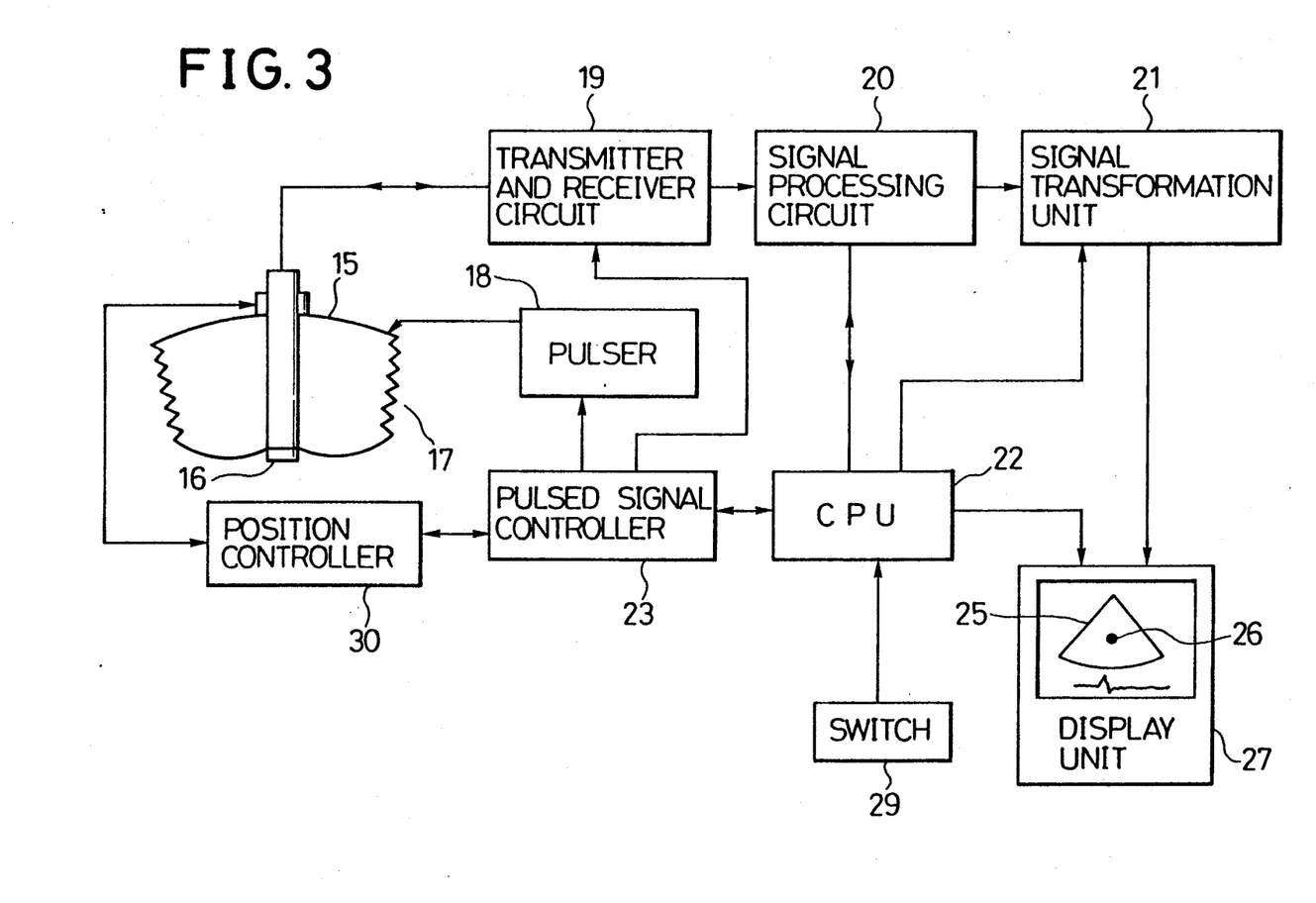
FIG. 3 is a schematic block diagram of one embodiment of a shock wave medical treatment apparatus according to the present invention.

Referring now to FIG. 3, there is shown one embodiment of a shock wave medical treatment apparatus according to the present invention, in the form of an ultrasonic medical treatment apparatus.

In this embodiment, the shock wave medical treatment apparatus comprises a shock wave applicator 17 including a shock wave transducer 15 for generating ultrasonic shock waves as shock waves for treatment and an imaging ultrasonic wave probe 16 for transmitting and receiving imaging ultrasonic waves, which will be described in greater detail below, a pulser 18 for activating the shock wave transducer 15 by supplying pulsed signals, a transmitter and receiver circuit 19 for activating the imaging ultrasonic wave probe 16 into sector scanning by supplying pulsed signals and receiving echo signals obtained by the imaging ultrasonic wave probe 16 as a result of sector scanning, a signal processing circuit 20 for converting output signals of the transmitter and receiver circuit into video signals by detecting amplitudes of the output signals, a signal transformation unit 21 such as a digital scan converter for performing signal transformation operation on output signals of the signal processing circuit 20, a CPU 22 for controlling elements of the apparatus, a pulsed signal controller 23 for controlling timings, amplitudes and frequencies of the pulsed signals at the pulser 18 and the transmitter and receiver circuit 19, a display unit 27 for displaying images such as those of a patient's body surface, an organ of interest, or concretion to be treated in the organ of interest, in a fan shaped imaging region 25 imaged by the imaging ultrasonic wave probe 16 along with a focal point marker 26 indicating a focal point of the ultrasonic shock waves generated by the shock wave transducer 15 and other information, a switch 29 for activating the supply of the pulsed signals by the pulser 18 to the shock wave transducer 15, and a position controller 30 for controlling a relative position of the shock wave transducer 15 with respect to the imaging ultrasonic wave probe 16.

Referring now to FIGS. 4 to 9, a detailed configuration of the shock wave applicator 17 will be described.

Figure 4:
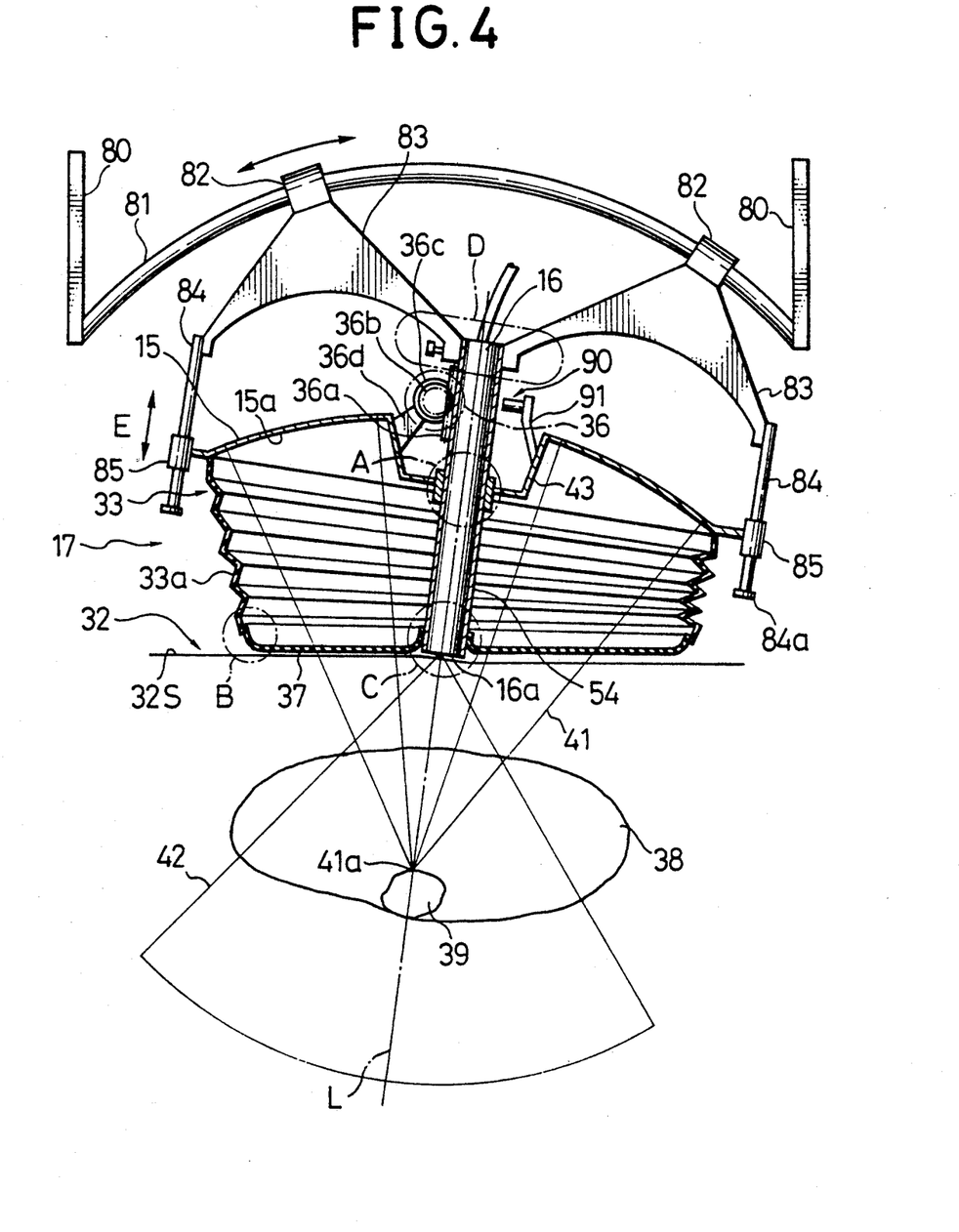
FIG. 4 is a detailed cross sectional view of a shock wave transducer in the apparatus of FIG. 3.

As shown in FIG. 4, the shock wave applicator 17 comprises the shock wave transducer 15 for generating the ultrasonic shock wave for treating an object to be treated, such as a concretion in an organ, from its constantly curved shock wave generating surface 15a equipped with a concave oscillator, with the focal point 41a located inside the patient 32, which has a central aperture, a water bag 33 as an acoustic coupler which is filled with water for propagating the ultrasonic shock waves from the shock wave transducer 15 to the patient 32 and which is attached to the shock wave transducer 15 on the shock wave generating surface 15a side, and the imaging ultrasonic wave probe 16 having an array of minute oscillator elements at a bottom face 16a for taking images in a region to be treated 42 including the focal point 41a by transmitting and receiving imaging ultrasonic waves with the bottom face 16a contacting the body surface 32S of the patient 32, which is located on a line L joining a center of the central aperture and the focal point 41a.

In this shock wave applicator 17, the imaging ultrasonic wave probe 16 is housed inside a cylindrical housing pipe 54 made of stainless steel which has an inner diameter slightly larger than an outer diameter of the imaging ultrasonic wave probe 16, and at the central aperture of the shock wave transducer 15 a cup shaped connecting member 43 having a slightly larger inner diameter than an outer diameter of the housing pipe 54 for supporting the shock wave transducer 15 with respect to the housing pipe 54 is provided around the housing pipe 54.

This shock wave applicator 17 is equipped with a tilting mechanism for the shock wave transducer 15 and the imaging ultrasonic wave probe 16 so that the shock wave transducer 15 and the imaging ultrasonic wave probe 16 can be tilted to a desired direction toward the patient 32. The tilting mechanism comprises a couple of symmetrically arranged connectors 83, each of which having a first guide 82 at a top which is slidably engaged to a circular guide rail 81. The circular guide rail 81 is suspended by a suspension frame 80 which can suspend the entire shock wave applicator 17, and is curved such that it has a shape of a part of circle centered around a middle of the bottom face 16a of the imaging ultrasonic wave probe 16. Each connector 83 has two bottom ends one of which is connected to a top end portion of the housing pipe 54 while another one of which is connected to a vertical guide rail 84 provided parallel to the housing pipe 54 by the shock wave transducer 15. The shock wave transducer 15 is connected with the vertical rails 84 through second guides 85 attached at an edge of the shock wave transducer 15 which are slidably engaged with the vertical guide rails 84. Each of the vertical guide rails 84 has a stopper 84a at a bottom end to prevent the second guide 85 from disengaging off the vertical guide rail 84. Thus, by sliding the first guides 82 along the circular guide rail 81 manually, the shock wave transducer 15 and the imaging ultrasonic wave probe 16 can be tilted to a desired direction toward the patient 32, without changing a relative position of the shock wave transducer 15 with respect to the imaging ultrasonic wave probe 16. Also, a vertical plane in which the tilting takes place can be rotated by rotating the suspension frame 80 around.

Furthermore, between the connecting member 43 and the housing pipe 54, there is provided a driver unit 36 for moving the shock wave transducer 15 in a direction E with respect to the housing pipe 54. This driver unit 36 comprises a rack 36a fixed on a side face of the housing pipe 54, a pinion gear 36b to be engaged with the rack 36a, a motor 36c as a source of driving power whose driving axis is connected to the pinion gear 36b, and a supporting member 36d for supporting the motor 36c with respect to the connecting member 43. The driver unit 36 moves the shock wave transducer 15 in a desired manner indicated by a control signal supplied from the position controller 30 appeared in FIG. 3.

Figure 5:
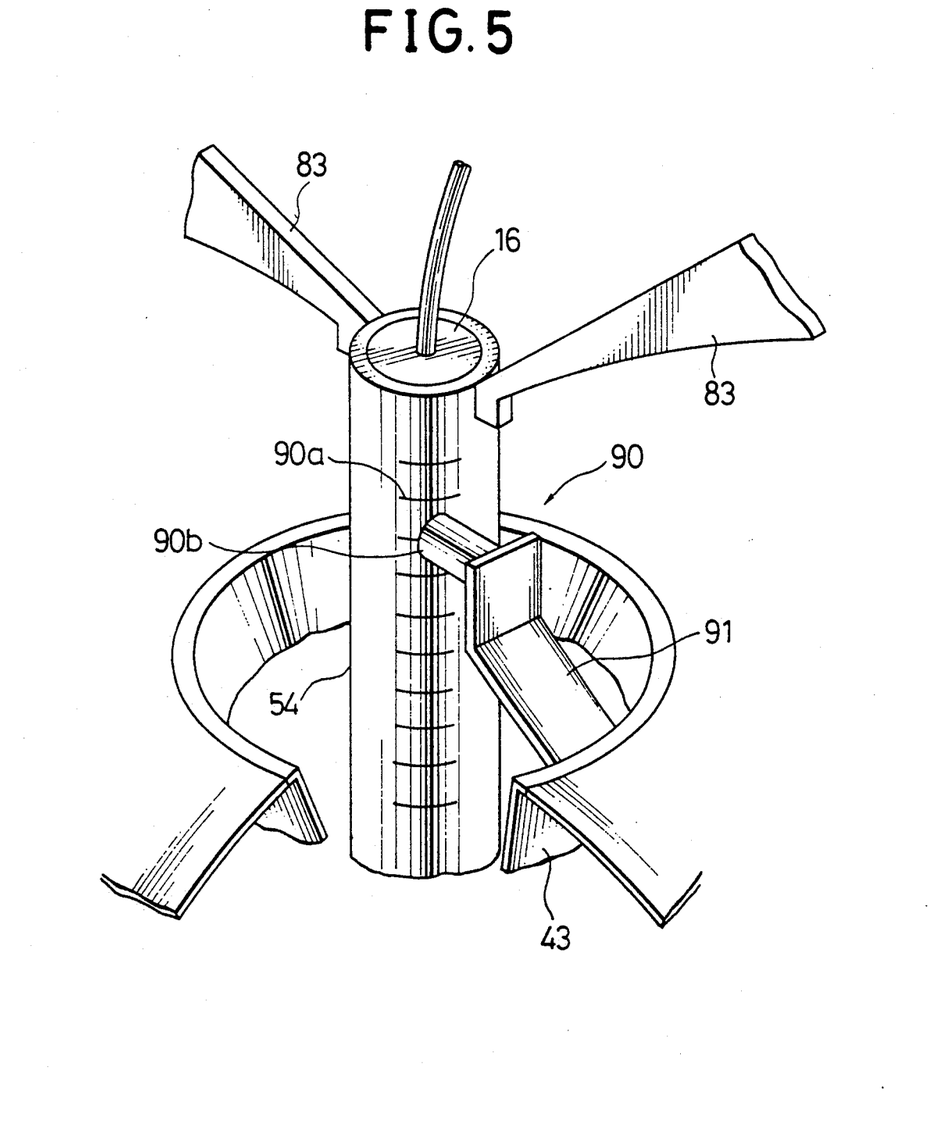
FIG. 5 is an enlarged cross sectional view of a position detection unit of the shock wave transducer of FIG. 4.

A position of the shock wave transducer 15 in the direction E with respect to the housing pipe 54 is detected by a position detection unit 90. As shown in FIG. 5, the position detection unit 90 comprises scale markings 90a provided on a side face of the housing pipe 54 for indicating prescribed intervals, a photo sensor 90b for reading the scale markings 90a, and a supporting element 91 for supporting the photo sensor 90b with respect to the connecting member 43.

The reading of the scale markings read by the photo sensor 90b is signaled to the position controller 30, which in turn controls rotation angle of the driving axis of the motor 36c such that the position of the shock wave transducer 15 with respect to the imaging ultrasonic wave probe 16 is controlled in a desired manner. When the motor 36c is not activated, the position of the shock wave transducer 15 is held fixed.

Figure 6:
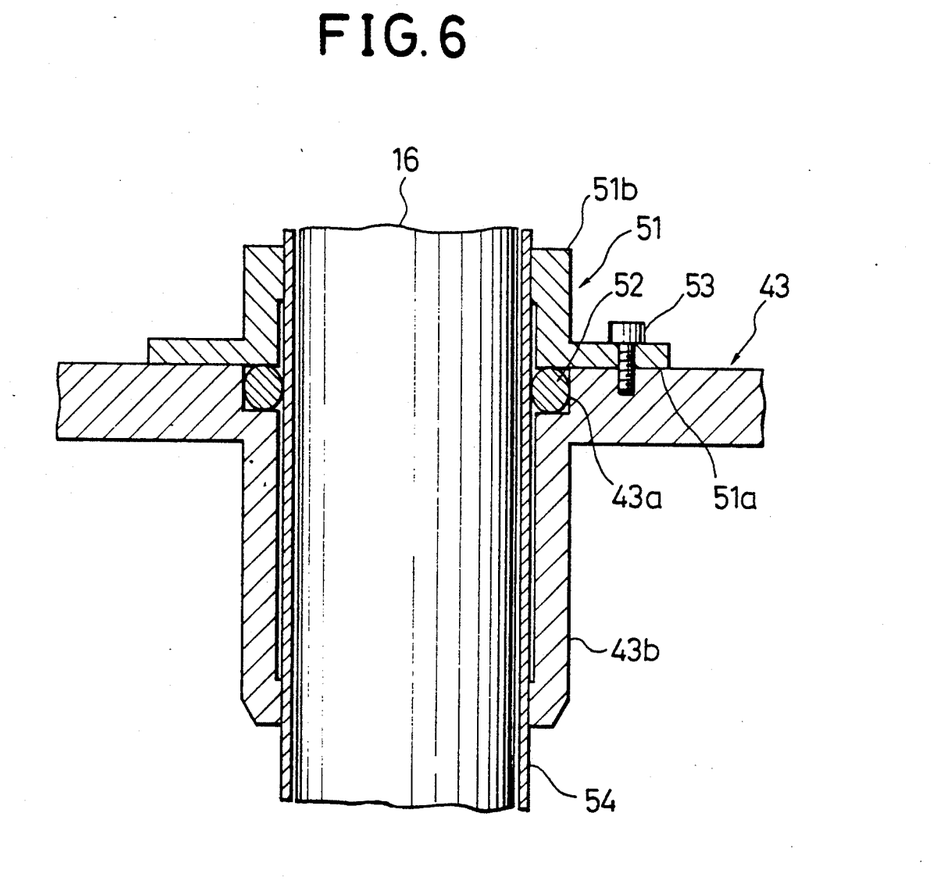
FIG. 6 is an enlarged cross sectional view of a portion A of the shock wave transducer of FIG. 4.

As shown in FIG. 6, in a vicinity of the central aperture A of the shock wave transducer 15, the connecting member 43 includes a lower pipe section 43b having a groove 43a for housing an O-ring 52 on an inner circumference side in contact with the housing pipe 54. The connecting member 43 is also equipped with a stopper member 51 having an upper pipe section 51b, a nut section 51a extending perpendicular to the upper pipe section 51b, and a bolt 53 to be engaged into the nut section 51a for fastening the stopper member 51 to a main part of the connecting member 43. The lower pipe section 43b and the upper pipe section 51b function to keep the housing pipe 54 from tilting with respect to the connecting member 43, while the O-ring 52 function to prevent leakage of the water contained inside the water bag 33 even when the shock wave transducer 15 is moved in the direction E.

The water bag 33 comprises a side face 33a in a form of bellows that can extend or contract in a certain range of angles around the direction E whose upper circumference is attached to the circumference of the shock wave transducer 15, and a bottom face 37 made of a thin film of rubber which has substantially equivalent acoustic impedance as the water.

Figure 7:
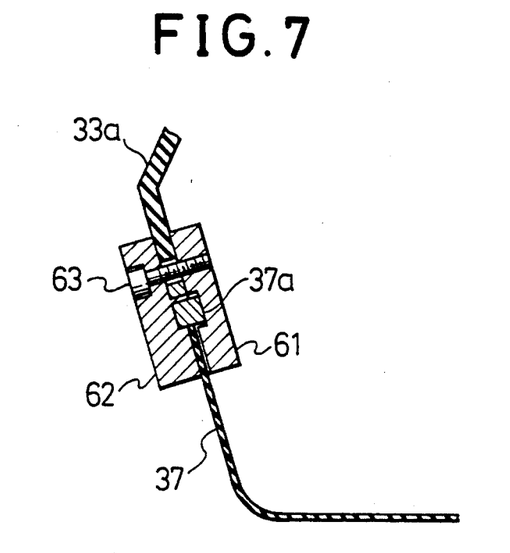
FIG. 7 is an enlarged cross sectional view of a portion B of the shock wave transducer of FIG. 4.

As shown in FIG. 7, the bottom face 37 has an outer reinforcement ring 37a formed around its outer rim, and the side face 33a and the bottom face 37 are connected by pinching an edge of the side face 33a and the reinforcement ring 37a together in between ring shaped fittings 61 and 62 fastened by a bolt 63.

Figure 8:
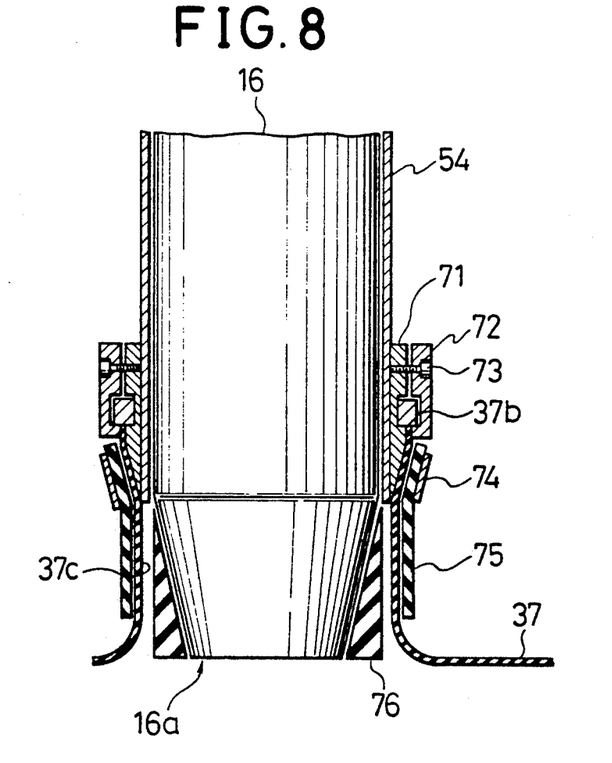
FIG. 8 is an enlarged cross sectional view of a portion C of the shock wave transducer of FIG. 4.

On the other hand, as shown in FIG. 8, the bottom face 37 also has an inner reinforcement ring 37b formed around its inner rim, and the bottom face 37 are fixed by pinching the reinforcement ring 37a in between ring shaped fittings 71 and 72 fastened by a bolt 73.

In addition, in order to wrap lightly around an end portion of the imaging ultrasonic wave probe 16 with an inner side wall portion 37c of the bottom face 37, there is an additional reinforcement member 75 made of rubber harder than that of the bottom face 37, at the inner side wall portion 37c, which is held fixed on the inner side wall portion 37c by a band 74, and an elastic ring shaped sponge 76 attached to the end portion of the imaging ultrasonic wave probe 16.

Thus, being made of thin film, the bottom face 37 may be ripped off, but in such a case the bottom face 37 can easily be replaced by separating the fittings 61 and 62 on the outer rim apart to remove the outer reinforcement ring 37a off, removing the water inside the water bag 33, separating the fittings 71 and 72 on the inner rim, and removing the band 74 on the inner side wall portion 37c.

Now, the imaging ultrasonic wave probe 16 has a fixed penetration depth, and this in turn determines a depth of the region to be treated. On the other hand, a distance between the body surface and the concretion differs for an adult patient and a child patient, even when the organ containing the concretion is identical. For this reason, it is preferable to use the imaging ultrasonic wave probe 16 of low frequency (3.75 MHz) for an adult patient in order to take image at deeper position, and to use the imaging ultrasonic wave probe 16 of high frequency (5 MHz) for a child patient in order to take image at a shallower position. The high frequency imaging ultrasonic wave probe 16 also has an advantage of being able to obtain high quality images. Similarly, it is preferable to select an appropriate one from more than one imaging ultrasonic wave probe 16 of different frequencies depending on depths of the concretion to be disintegrated. Also, it is preferable to select an appropriate one from more than one imaging ultrasonic wave probe 16 of different frequencies depending on physical constitution of the patient, such as the imaging ultrasonic wave probe 16 of low frequency for a fatty patient, and the imaging ultrasonic wave probe 16 of high frequency for a muscular patient.

Figure 9:
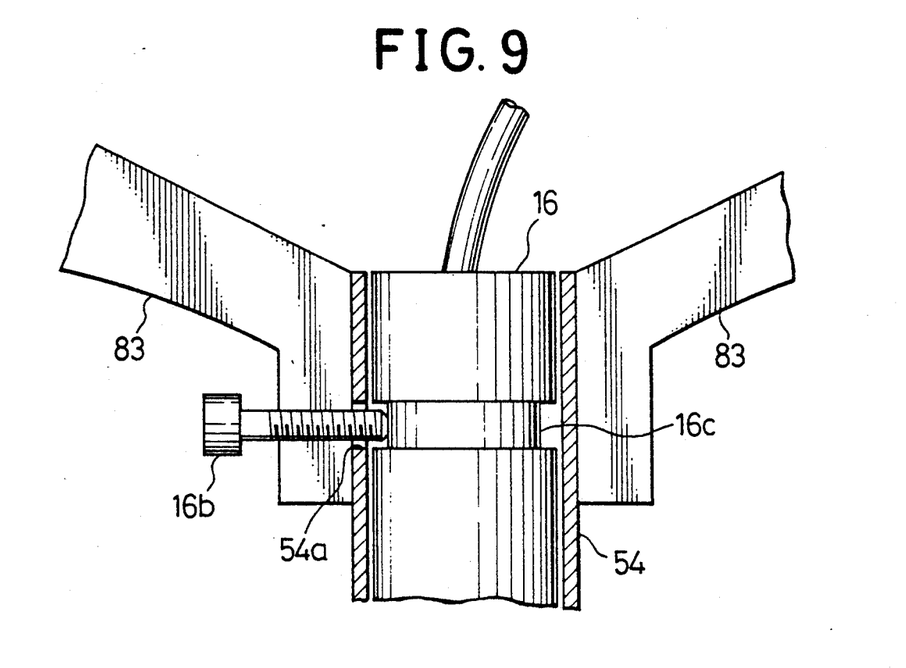
FIG. 9 is an enlarged cross sectional view of a portion D of the shock wave transducer of FIG. 4.

For this reason, in this embodiment, the imaging ultrasonic wave probe 16 is housed inside the housing pipe 54 so as to be easily changed by another. Moreover, in this embodiment, the imaging ultrasonic wave probe 16 is rotatable around its central axis. More specifically, as shown in FIG. 9, a clearance of about 0.5 to 1 mm is provided between the inner diameter of the housing pipe 54 and the outer diameter of the imaging ultrasonic wave probe 16 so that the imaging ultrasonic wave probe 16 can easily be inserted into the housing pipe 54. In addition, the imaging ultrasonic wave probe 16 has a groove 16c in a vicinity of its top end portion such that a bolt 16b can be fastened through a hole 54a provided on the housing pipe 54 into the groove 16c. When the bolt 16b is fully tightened the imaging ultrasonic wave probe 16 can be fixed at a desired position, whereas when the bolt 16 is only loosely tightened the imaging ultrasonic wave probe 16 can be rotated around its central axis.

Now, the operation of this embodiment of a shock wave medical treatment apparatus will be described for an exemplary case of treating a concretion 39 inside an organ 38 shown in FIG. 4.

The imaging ultrasonic wave probe 16 having an appropriate penetration depth for concretion 39 to be treated is selected in advance, installed into the the housing pipe 54, and fixed by means of the bolt 16b.

Then, the water bag 33 of the shock wave applicator 17 is placed over the body surface 32S of the patient 32 above the organ 38, with the imaging ultrasonic wave probe 16 contacting the body surface 32S.

Next, the imaging ultrasonic wave probe 16 is activated along with the transmitter and receiver circuit 19, the signal processing circuit 20, and the signal transformation unit 21, such that a tomographic image of the patient 32 is displayed on the display unit 27. Here, because the imaging ultrasonic wave probe 16 is contacting the body surface 32S, a very clear image without any influence of the water or the bottom face 37 of the water bag 33 is obtainable, and this helps a quick and easy apprehension of the concretion 39.

Next, the imaging ultrasonic wave probe 16 is operated to show the concretion 39 on the tomographic image displayed on the display unit 27. This operation may involve such maneuvering for obtaining a clearer image as tilting the imaging ultrasonic wave probe 16 by sliding the first guides 82 along the circular guiding rail 81, and rotating the imaging ultrasonic wave probe 16 around the line L by slightly loosening the bolt 16b.

On the fan shape imaging region 25 of the display unit 27, a relative position of the focal point 41a of the shock wave transducer 15 with respect to the imaging ultrasonic wave probe 16 is indicated in real time in a form of the marker 26 according to the signals from the position detection unit 90 transmitted through the CPU 22 and the signal transformation unit 21. When the concretion 39 is displayed on the tomographic image, the position controller 30 is operated to move the shock wave transducer 15 in the direction E until the marker 26 and the concretion 39 coincide on the display unit 27. Here, because the bottom face 16a of the imaging ultrasonic wave probe 16 is located on the line L joining a center of the central aperture and the focal point 41a, the concretion 39 can be displayed at a center of the displayed image, and this also helps a quick and easy apprehension of the concretion 39. Also, because the relative position of the shock wave transducer 15 with respect to the imaging ultrasonic wave probe 16 is adjustable, the treatment operation become easier.

Next, the switch 29 is operated to send the control signal to the pulser 18 through the CPU 22 and the pulsed signal controller 23, such that the pulsed signals are transmitted from the pulser 18 to the shock wave transducer 15 and the powerful ultrasonic shock waves are generated from the shock wave transducer 15 toward the concretion 39 located at the position indicated by the marker 26 on the display unit 27 to disintegrate the concretion 39. Such a shock wave application is repeated as many times as necessary to completely disintegrate the concretion 39.

As described, in this embodiment of a shock wave medical treatment apparatus, a quick and easy apprehension of the concretion 39 is possible because a very clear image without influences of the water or the bottom face 37 of the water bag 33 is obtainable as a result of the fact that the imaging ultrasonic wave probe 16 is contacting the body surface 32S.

A clear image is obtainable also because the imaging ultrasonic wave probe 16 is rotatable around its central axis.

Moreover, the imaging ultrasonic wave probe 16 is housed inside the housing pipe 54 so that one having an appropriate penetration depth can quickly and easily be installed.

In addition, since the imaging ultrasonic wave probe 16 is completely separated from the water in the water bag 33, the damaging of the imaging elements due to wetting of the imaging elements through the lenses covering the imaging elements, which has been accompanying the change of the probe in a conventional shock wave medical treatment apparatus, can be prevented.

Also, because of the water bag 33 which functions as an acoustic coupler, the shock wave can be transmitted efficiently.

Also, because the side face of the water bag 33 is a bellows, the water bag 33 can easily be stretched or contracted in a vertical direction, and the adjustment of the relative position of the shock wave transducer 15 with respect to the imaging ultrasonic wave probe 16 become easier. Here, the leakage of the water from the water bag 33 in moving the shock wave transducer 15 is prevented by the O-ring 52 provided between the connecting member 43 and the housing pipe 54.

Also, because the focal point 41a of the ultrasonic shock wave from the shock wave transducer 15 is indicated on the display unit 27 by the marker 26, accurate treatment can be performed easily.

Now, there are several variations of the embodiment described above possible.

Figure 10:
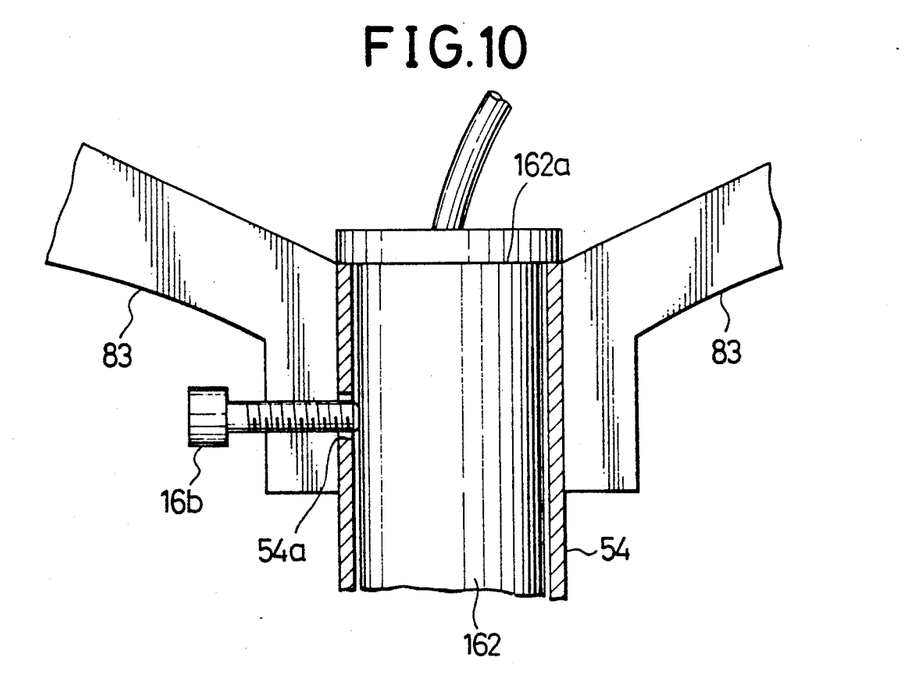
FIG. 10 is an enlarged cross sectional view of an alternative configuration for the portion D shown in FIG. 9.

First of all, a configuration of a portion D in FIG. 4, which is shown in detail in FIG. 9, may be altered to that shown in FIG. 10. In this alternative configuration, the imaging ultrasonic wave probe 162 is equipped with a stopper 162a at its top end, which replaces the groove 16c of the above embodiment. Thus, when the imaging ultrasonic wave probe 162 is inserted into the housing pipe 54, the position of the imaging ultrasonic wave probe 162 is determined as the stopper 162a abuts the top edge of the housing pipe 54. The imaging ultrasonic wave probe 162 can be fixed, or made free to rotate by tightening or loosening the bolt 16b as in the above embodiment.

Also, the shock wave transducer 15 may be of an electromagnetic induction type shock wave generator instead of a generator using oscillator elements as in the above embodiment.

Figure 11:
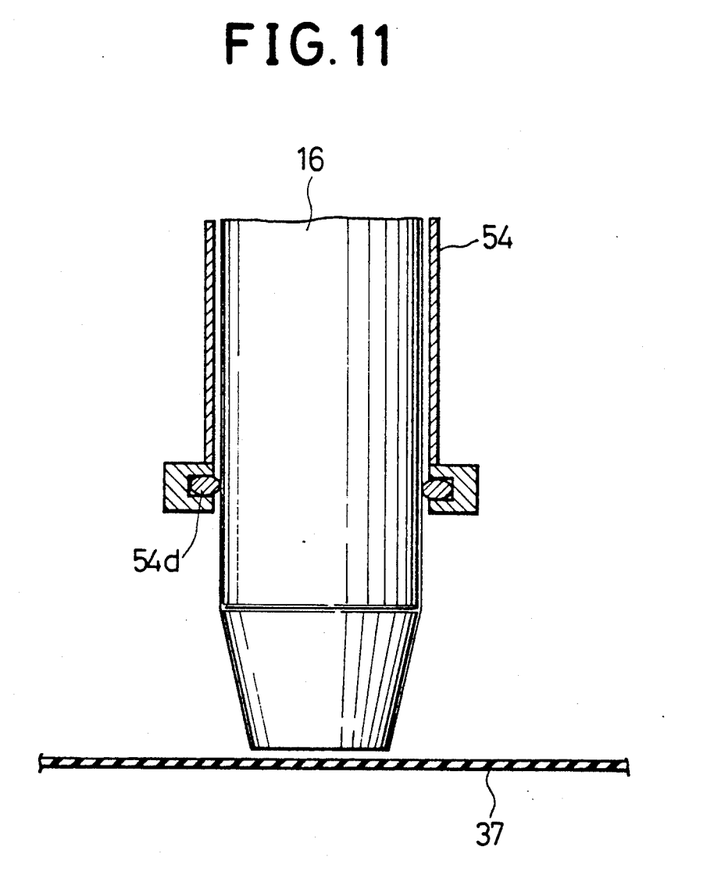
FIG. 11 is an enlarged cross sectional view of an alternative configuration for the portion C shown in FIG. 8.

Also, a configuration of a portion C in FIG. 4, which is shown in detail in FIG. 8, may be altered to that shown in FIG. 11. In this alternative configuration, the bottom face 37 of the water bag 33 is extended to cover the bottom face 16a of the imaging ultrasonic wave probe 16, while at the lower end of the housing pipe 54, which is shorter than the imaging ultrasonic wave probe 16 in this case, there is provide an O-ring 54d for preventing the water from entering into the housing pipe 54, which is contacting the side face of the imaging ultrasonic wave probe 16. In this case, since the water that comes between the imaging ultrasonic wave probe 16 and the body surface 32S possesses an acoustic impedance close to that of a human body, the efficient transmission of the ultrasonic wave is possible.

Also, the position detection unit 90 of the above embodiment may be replaced by a potentiometer of variable resistor type provided in conjunction with the pinion gear 36b.

Also, instead of moving the shock wave transducer 15, the imaging ultrasonic wave probe 16 may be made to be movable with respect to the shock wave transducer 15.

Besides these, many modifications and variations of the above embodiments may be made without departing from the novel and advantageous features of the present invention. Accordingly, all such modifications and variations are intended to be included within the scope of the appended claims.

What is claimed is:

1. A shock wave applicator for a shock wave medical treatment apparatus, comprising:

shock wave transducer means for generating shock waves with their focal point inside a body to be treated, the shock wave transducer means having an aperture at its center;

imaging ultrasonic wave probe means for taking images of the body to be treated containing the focal point of the shock waves;

acoustic coupler means, arranged to be in contact with the shock wave transducer means, for propagating the shock waves between the shock wave transducer means and the body to be treated, the acoustic coupler means having a central hole on a bottom surface;

housing pipe means disposed in the aperture of the shock wave transducer means and central hole of the acoustic coupler means and placed on a line joining the focal point of the shock waves and the center of the aperture of the shock wave transducer means, for exchangeably holding the imaging ultrasonic wave probe means inside of the housing pipe means, where an interior of the acoustic coupler means and the imaging ultrasonic wave probe means held inside the housing pipe means are completely separated by the housing pipe means; and means for sliding the shock wave transducer means along the housing pipe means while the imaging ultrasonic wave probe means is held inside the housing pipe means.

2. The apparatus of claim 1, wherein the means for sliding changes the relative position of the shock wave transducer means and the imaging ultrasonic wave probe means with respect to each other or the body to be treated.

3. The apparatus of claim 1, wherein the acoustic coupler means comprises a water bag filled with water capable of stretching and contracting at least in a direction along the line joining the focal point of the shock waves and the center of the aperture of the shock wave transducer means.

4. The apparatus of claim 1, wherein a bottom face of the imaging ultrasonic wave probe means and the bottom face of the acoustic coupler means form an externally exposed surface which is adapted to directly contact a surface of the body to be treated.

5. The apparatus of claim 1, wherein the housing pipe means holds the imaging ultrasonic wave probe means to be rotatable around a central axis of the imaging ultrasonic wave probe means.

6. The apparatus of claim 5, wherein the housing pipe means includes means for preventing the imaging ultrasonic wave probe from rotating.

* * * * *